United States Patent [19]

Tsutsumi et al.

[11] Patent Number: 4,998,377

[45] Date of Patent: Mar. 12, 1991

[54] METHOD OF KILLING PESTS

[75] Inventors: Teruyuki Tsutsumi; Tetsunori Sato; Akira Arita, all of Mihara, Japan

[73] Assignee: Teijin Chemicals, Ltd., Tokyo, Japan

[21] Appl. No.: 506,239

[22] Filed: Apr. 9, 1990

[30] Foreign Application Priority Data

Apr. 10, 1990 [JP] Japan ................................. 1-88097

[51] Int. Cl.$^5$ ............................................. A01M 13/00
[52] U.S. Cl. ........................................ 43/125; 422/32; 422/37; 426/318; 426/320
[58] Field of Search ................... 43/125, 124; 422/32, 422/37; 426/318, 320

[56] References Cited

U.S. PATENT DOCUMENTS

| | | | |
|---|---|---|---|
| 2,321,023 | 6/1943 | Goodhue et al. | 43/125 |
| 2,570,917 | 10/1951 | Calfee | 43/125 |
| 2,750,252 | 6/1956 | Sullivan et al. | 43/125 |
| 4,200,656 | 4/1980 | Cohen | 426/320 |
| 4,756,117 | 7/1988 | Friemel | 43/125 |

FOREIGN PATENT DOCUMENTS

| | | | |
|---|---|---|---|
| 7189628 | 5/1981 | Japan | 43/125 |
| 3215503 | 9/1988 | Japan | 43/125 |
| 1191046 | 7/1983 | U.S.S.R. | 43/125 |

Primary Examiner—Richard K. Seidel
Assistant Examiner—James Miner
Attorney, Agent, or Firm—Sherman and Shalloway

[57] ABSTRACT

An improved method of fumigating fresh plants on which pests are parasitic. The method comprises maintaining the fresh plants in a gaseous atmosphere composed of 10 to 50 mg/liter of methyl bromide, 0.01 to 10 mg/liter of hydrogen phosphide, and 1 to 50% by volume of carbon dioxide. The method can surely kill the pests on the plants without causing phytotoxicity.

3 Claims, No Drawings

METHOD OF KILLING PESTS

BACKGROUND OF THE INVENTION

1. Field of the Invention

This invention relates to a method of killing pests parasitic on fresh plants, and more specifically, to a method of killing pest parasitic on fresh plants by fumigation.

2. Description of the Prior Art

Fumigation with methyl bromide or hydrogen phosphide has been practised previously to kill pests parasitic on fresh plants, particularly on imported fresh plants. However, this method has many problems to be solved. For example, fumigation with methyl bromide is little effective on scales and mites parasitic on banana and lemon, and cannot be applied to fresh plants having strong sensitivity to methyl bromide, such as lettuce and cut flowers of chrysanthemum. Fumigation with hydrogen phosphide requires a long period of time of 3 or more days, and is useless on many fresh plants which are required to be fresh. A method for reducing phytotoxicity of methyl bromide in an ordinary fumigation concentration (30 to 50 mg/liter) by mixing 10 to 40% by volume of carbon dioxide with it (Results of Test of Fumigation of Carbon Dioxide-Containing Methyl Bromide, 1986 to 1989, Japan Association of Fumigation Technology) and a method of increasing the pesticidal effect by using a gaseous mixture of 0.06 to 0.012 mg/liter of hydrogen phosphide and 4 to 20% by volume of carbon dioxide [J. Slored Prod. Res. 11 9-15 (75) KP (Kashi E. J. Bond] were proposed. These gaseous mixtures containing carbon dioxide show a considerable improvement in pesticidal effect, but the first-mentioned method does not show any appreciable effect of reducing the phytotoxicity, and according to the latter method, no drastic shortening of the fumigation period can be expected.

SUMMARY OF THE INVENTION

It is an object of this invention to provide a method of fumigation which does not cause phytotoxicity to fresh plants and show a sure pesticidal effect on many pests parasitic on plants.

According to this invention, the above object is achieved by a method of killing pests parasitic on fresh plants, which comprises maintaining the fresh plants on which pests are parasitic in an atmosphere of a gaseous mixture composed of 10 to 50 mg/liter of methyl bromide, 0.01 to 10 mg/liter of hydrogen phosphide and 1 to 50% by volume of carbon dioxide for at least 1 hour.

DETAILED DESCRIPTION OF THE INVENTION

If the amount of methyl bromide does not reach 10 mg/liter, no sufficient pesticidal effect can be obtained, and if it is larger than 50 mg/liter, it becomes phytotoxic. If the amount of hydrogen phosphide does not reach 0.01 mg/liter, no sufficient pesticidal effect can be obtained. The use of hydrogen phosphide in an amount of more than 10 mg/liter is meaningless since its effect is saturated. When the amount of carbon dioxide gas does not reach 1% by volume, no sufficient pesticidal effect can be obtained. The use of more than 50% by volume of carbon dioxide is meaningless, because its effect is no longer increases.

Fumigation in accordance with the method of this invention may be performed, for example, by feeding a gaseous mixture of predetermined amounts of methyl bromide, hydrogen phosphide and carbon dioxide into a closed fumigation vessel from outside; or filling a timed jetting device with predetermined amounts of methyl bromide, hydrogen phosphide and carbon dioxide, and providing it in a fumigation vessel as enclosed in a bomb or a can, and jetting out the gaseous mixture after a predetermined time; or filling a timed jetting device with methyl bromide and/or hydrogen phosphide, providing it in a fumigation vessel as enclosed in a bomb or a can, jetting out the gas after a predetermined time, and feeding another component from outside. When methyl bromide, hydrogen phosphide and carbon dioxide are to be supplied from outside, they may be fed simultaneously or in any sequence. Preferably, carbon dioxide is fed in the first place. Hydrogen phosphide can be generated by giving moisture (water) or an acid to a metal phosphide such as aluminum phosphide or magnesium phosphide. Since depending upon the generating conditions, fire may occur, the operation of generating hydrogen phosphide is preferably carried out in an incombustible gaseous mixture such as carbon dioxide, nitrogen gas or methyl bromide. It is also preferable to include a fire inhibitor into the metal phosphide in advance. Hydrogen phosphide may be used as filled in a container such as a bomb or a can. In this case, it may be filled as a mixture with an incombustible gas such as carbon dioxide, nitrogen gas or methyl bromide.

The method of this invention brings about the excellent advantage that by using a mixture of specific amounts of methyl bromide, hydrogen phosphide and carbon dioxide, many pests parasitic on fresh plants can be surely killed while suppressing phytotoxicity.

Examples of fresh plants which can be fumigated by the method of this invention without causing phytotoxicity include fresh fruits such as banana, pineapple, lemon, grapefruit, orange, kiwi fruit, and avocado; vegetables such as lettuce, okra, asparagus and garden pea; cut flowers such as chrysanthemum, carnation, orchid and fern; bulbiferous plants such as tulip and sword lily; and seedlings, seedling tree, saplings, cuttings and seeds of orchid, for example.

Examples of pests which can be surely killed by the method of this invention include Order Thysanoptera such as *Thrips tabachi;* Order Hemiptera such as aphids, *Nazasra antennata* and scales; Order Lepidoptera such as *Archips xylostreana, Plutella xylostella, Hellula undalis,* and *Mamestra brassicae;* Order Coleoptera such as *Phyllotrata strialata;* Order Diptera such as *Ceratitis capitata;* Order Coleoptera such as *Cylas formicarius* and *Ficiphagus goliatoses;* and Order acsarina such as *Tetranychus kanzawai, Rhizoglyphus echinopus, Hemitarsonylmus latus* and *Tecranychus urcae.* It is not clear why the gaseous mixture used in this invention has reduced phytotoxicity on fresh plants. It is presumed that as a result of using hydrogen phosphide and carbon dioxide together, the reduction of the amount of methyl bromide adsorbed on fresh plants and the effect of the combined use of the above compounds on physiological activities such as the absorption of fresh plants and an enzyme for ethylene synthesis synergistically act advantageously to prevent phytotoxicity of methyl bromide.

The following examples illustrate the present invention specifically. The concentrations of methyl bromide, hydrogen phosphide and carbon dioxide are based on the inside volume of the fumigation vessel irrespective of the presence of the plants to be fumigated.

REFERENTIAL EXAMPLE (Preparation of a Gaseous Mixture)

Two liters of carbon dioxide (corresponding to 20% by volume) was added to a 10-liter fumigation vessel. To avoid exertion of pressure on the vessel, air was replaced by carbon dioxide. Then, while 47.2 ml (corresponding to 20 mg/liter) of methyl bromide gas was added, 19.8 ml (3 mg/liter) of hydrogen phosphide gas was added. They were fully mixed. The gaseous mixture was analyzed by gas chromatography, and found to be composed of 21 mg/liter of methyl bromide, 3 mg/liter of hydrogen phosphide, and 21% by volume of carbon dioxide. This mixing method did not cause burning of hydrogen phosphide gas.

The gaseous mixtures used in the following examples were prepared by the above method.

EXAMPLE 1 AND COMPARATIVE EXAMPLE 1

One bunch of banana, 10 lemons, two heads of lettuce and 10 cut flowers of chrysanthemum were separately put in a 10-liter fumigation vessel and were fumigated at 10° C. for 2 hours with a gaseous mixture composed of 30 mg/liter of methyl bromide, 5 mg/liter of hydrogen phosphide and 20% by volume of carbon dioxide. The presence of phytotoxicity and its degree were evaluated. The results are shown in Table 1.

For comparison, the above procedure was repeated except that a gaseous mixture composed of 30 mg/liter of methyl bromide and 20% by volume of carbon dioxide was used. The results are shown in Table 1.

The presence of phytotoxicity and its degree were evaluated after storage at 10° C. for one month for banana and lemons, and after storage for 2 weeks at 20° C. for lettuce and cut flowers of chrysanthemum by comparing changes in the appearance of the fumigated plants with those not fumigated.

TABLE 1

|  | Example 1 | | | Comparative Example 1 | |
| --- | --- | --- | --- | --- | --- |
| Mixture | Methyl bromide | Hydrogen phosphide | $CO_2$ | Methyl bromide | $CO_2$ |
| Mixing concentration | 30 mg/l | 5 mg/l | 20 vol. % | 30 mg/l | 20 vol. % |
| Fumigation time (hr) | | 2 | | | 2 |
| Fumigation temp. (°C.) | | 10 | | | 10 |
| Degree of Phytotoxicity | | | | | |
| banana | | − | | | + |
| lemon | | − | | | + |
| lettuce | | − | | | + |
| Cut flowers of chrysanthemum | | − | | | ++ |

Note Standards of evalution
−: No phytotoxicity
+: Slight phytotoxicity
++: Considerably heavy phytotoxicity

EXAMPLE 2 AND COMPARATIVE EXAMPLES 2 AND 3

In a 10-liter fumigation vessel were placed fifty heads each of *Thrits talmi, Tribolium confusum, Sitobhilus zeamais* and *Planococcus kraunhiae* fed with plants or an aritifical feed and released into cages. The pests were fumigated at 10° C. for 4 hours with a gaseous mixture composed of 10 mg/liter of methyl bromide, 0.5 mg/liter of hydrogen phosphide and 20% by volume of carbon dioxide. The pesticidal effect was evaluated. The results are shown in Table 2.

For comparison, the above procedure was repeated except that a gaseous mixture composed of 10 mg/liter of methyl bromide and 20% by volume of carbon dioxide (Comparative Example 2) or a gaseous mixture composed of 5 mg/liter of hydrogen phosphide and 20% by volume of carbon dioxide (Comparative Example 3) was used. The results are shown in Table 2.

The pesticidal effect was evaluated by determining the kill ratio of the pests during storage for 72 hours after fumigation.

TABLE 2

|  | Example 2 | | | Comparative Example 2 | | Example 3 | |
| --- | --- | --- | --- | --- | --- | --- | --- |
| Mixture | Methyl bromide | Hydrogen phosphide | $CO_2$ | Methyl bromide | $CO_2$ | Hydrogen phosphide | $CO_2$ |
| Mixing concentration | 10 mg/l | 0.5 mg/l | 20 vol. % | 10 mg/l | 20 vol. % | 5 mg/l | 20 vol. % |
| Fumigation time (hr) | | 2 | | 4 | | 4 | |
| Fumigation temp. (°C.) | | 10 | | 10 | | 10 | |
| Results | | | | | | | |
| A | | O | | Δ | | Δ | |
| B | | O | | X | | Δ | |
| C | | O | | Δ | | X | |

TABLE 2-continued

|   | Example 2 | Comparative Example 2 | Example 3 |
|---|---|---|---|
| D | O | X | X |

Note
A : thrits talmi
B : tribolium confusum
C : sitobhilus zeamais
D : Planococcus Kraunhiae
Standards of evaluation of pesticidal effect
O : more than 99%, Δ : 99–80%, X : less than 80%

We claim:

1. A method of killing pests parasitic on fresh plants, which comprises maintaining the fresh plants in a mixed gaseous atmosphere composed of 10 to 50 mg/liter of methyl bromide, 0.01 to 10 mg/liter of hydrogen phosphide and 1 to 50% by volume of carbon dioxide for at least 1 hour.

2. The method of claim 1 in which the fresh plants are banana, lemon, lettuce or cut flowers of chrysanthemum.

3. The method of claim 1 in which the pest is *Thrits talmi, Tribolium confusum, Sitobhilus zeamais* or *Planococcus kraunhiae.*

UNITED STATES PATENT AND TRADEMARK OFFICE
CERTIFICATE OF CORRECTION

PATENT NO. : 4,998,377

DATED : March 12, 1991

INVENTOR(S) : TERUYUKI TSUTSUMI, ET AL.

It is certified that error appears in the above-identified patent and that said Letters Patent is hereby corrected as shown below:

ON THE TITLE PAGE

At [30] Foreign Application Priority Data, "April 10, 1990 [JP]" should read --April 10, 1989 [JP]--.

Signed and Sealed this

Eighth Day of June, 1993

Attest:

MICHAEL K. KIRK

Attesting Officer

Acting Commissioner of Patents and Trademarks